(12) United States Patent
Gerstel

(10) Patent No.: US 8,808,629 B2
(45) Date of Patent: Aug. 19, 2014

(54) TRANSFER UNIT FOR ANALYSIS DEVICES

(75) Inventor: Joachim Gerstel, Mülheim an der Ruhr (DE)

(73) Assignee: Joint Analytical Systems GmbH, Moers (DE)

( * ) Notice: Subject to any disclaimer, the term of this patent is extended or adjusted under 35 U.S.C. 154(b) by 605 days.

(21) Appl. No.: 13/122,959

(22) PCT Filed: Sep. 14, 2009

(86) PCT No.: PCT/EP2009/061858
§ 371 (c)(1),
(2), (4) Date: Jun. 14, 2011

(87) PCT Pub. No.: WO2010/040619
PCT Pub. Date: Apr. 15, 2010

(65) Prior Publication Data
US 2011/0305608 A1    Dec. 15, 2011

(30) Foreign Application Priority Data
Oct. 6, 2008  (DE) .......................... 10 2008 037 416

(51) Int. Cl.
*G01N 30/16* (2006.01)
(52) U.S. Cl.
USPC ............... 422/89; 73/23.35; 73/23.41; 96/89; 96/105; 250/288
(58) Field of Classification Search
USPC ....... 95/89; 96/105; 73/23.35–23.42; 422/89; 250/288
See application file for complete search history.

(56) References Cited

U.S. PATENT DOCUMENTS

| 4,766,760 | A |   | 8/1988  | Poshemansky et al. |
|-----------|---|---|---------|-------------------|
| 5,310,681 | A |   | 5/1994  | Rounbehler et al. |
| 5,702,671 | A | * | 12/1997 | Gerstel ........................ 422/544 |
| 6,055,845 | A |   | 5/2000  | Gerstel et al. |
| 6,223,584 | B1|   | 5/2001  | Mustacich et al. |

FOREIGN PATENT DOCUMENTS

| DE | 3400458     | 7/1985  |
| DE | 3448091     | 7/1986  |
| DE | 10130382    | 10/2002 |
| EP | 0451566     | 10/1991 |
| EP | 1 262 772   | 4/2002  |
| WO | WO 97/10888 | 3/1997  |

OTHER PUBLICATIONS

Dr. Gerhard Schomburg, Probenaufgabe in der Kapillargaschromatographie, DE journal Labo Kennziffer Fachzeitschrift fur Labortechnik, Edition Jul. 1983, pp. 37-46.

* cited by examiner

*Primary Examiner* — Jan Ludlow
(74) *Attorney, Agent, or Firm* — Thorpe North & Western LLP

(57) ABSTRACT

The invention relates to a transfer unit for analysis devices, containing a tube-shaped assembly which can be heated by an electric heater in a programmed manner, a tube (6) which is arranged in the sample chamber (18) and into which the end of a gas chromatographic separating column can be inserted at the end of said tube, and means for introducing carrier gas into the tube (6), said transfer unit being characterized in that a temperature sensor (8) is arranged in the ring chamber (5) between the inner wall of the assembly and the evaporator tube (6). The transfer unit can be a sample introduction device for a gas chromatograph having a sample introduction head (18), and the assembly can be a sample introduction chamber in which an evaporator tube is provided, wherein the end of a gas chromatographic separating column can be inserted into the end facing away from the sample introduction head (18).

16 Claims, 1 Drawing Sheet

TRANSFER UNIT FOR ANALYSIS DEVICES

TECHNICAL FIELD

The invention relates to a transfer unit for analytic instruments, comprising a tubular, cartridge-type assembly group in the form of a sampling chamber adapted to be heated by an electric heater according to a program, a liner inside said tubular assembly group adapted to receive the end of a gas chromatographic separating column at its end, and means for inserting carrier gas into the tube.

In particular, a transfer unit for analytic instruments in the present case is here understood to be sample inlets for example for gas chromatography, heated cooling traps and transfer lines for fluids.

PRIOR ART

Sampling chambers are, for example, known from a publication by Schomburg "Probenaufgabe in der Kapillargaschromatographie" in the DE journal "LABO Kennziffer Fachzeitschrift für Labortechnik", Edition July 1983, pages 37 to 46 and DE 34 48 091 C3.

For introducing a liquid sample in a gas chromatograph usually the sample is dissolved in a solvent in order to obtain suitable amounts. The dissolved sample is injected with an injection needle through a sampling head with a septum or a heated valve into the carrier gas flow. The carrier gas flow carries the sample and the solvent through a liner. The liner, which normally consists of glass, sits in a sampling chamber heated by a heater. In the publication in LABO this heater is an air heater, where the air is heated by a heating coil.

In DE 34 48 091 C3 the sampling chamber is a tube surrounded by a heating coil. The liner sits in the middle of the tube shaped sampling chamber. An annular space is formed between the liner and the sampling chamber. The sampling chamber and thereby the liner are adapted to be heated according to a program. In "split"-operation, at first the highly volatile solvent is evaporated. This evaporated solvent flows through the liner and the annular space and is removed through the split outlet. Subsequently, the sample itself is evaporated by a "ballistic" heating to higher temperatures. A separating column, preferably a capillary column requiring and processing only small amounts of sample, extends into the end of the liner opposite to the inlet with its inlet end. The sample is carried by the carrier gas into the separating column. The separating column is heated according to a temperature program. As a larger volume of sample gas is generated in the liner a focusing of the sample is effected at the inlet of the separating column. The temperature of the separating column is maintained low at first. This causes a small carrier velocity of all components of the sample in the separating column. A plug of sample gas is formed at the inlet of the separating column. Upon increasing temperature in the separating column the differences of volatility of the various sample components become more apparent and cause different carrier velocities and thereby a resolution of the sample in peaks which separately appear at the outlet of the separating column.

The temperature in the liner should be as uniform as possible along the length of the liner. It should follow the desired program as exactly as possible and with as little delay as possible. This also requires an exact measurement of the temperature. These conditions are not or not sufficiently fulfilled with the described prior art. The heating with hot air, as shown in the publication LABO is slow. The same applies for the heating according to DE 34 48 091 C3. In the latter publication a relatively rough heating coil heats the massive sampling chamber causing a temperature compensation and ensuring a relatively constant temperature along its length. The constant temperature is traded for thermal inactivity. None of the cited documents deals with the temperature measurement or temperature control.

EP 12 62 772 A2 discloses a temperature controlled injector for gas chromatographs with a injector tube which is arranged in a cooled receiving tube. This receiving tube consists of well conducting material which is electrically isolated towards the outside. The temperature sensor of the assembly is on the outside.

WO 97/10888 discloses a packed pre-column heated by means of a heating coil. The heating coil is arranged between two quartz tubes which are held in their position by caps. A temperature sensor not described in detail can be arranged between the pre-column and the inner quartz tube.

DISCLOSURE OF THE INVENTION

It is an object of the invention to provide a sample inlet of the above mentioned kind in such a way that the precise application of a given temperature program in the liner is ensured.

According to the invention, this object is achieved by an assembly according to claim 1. In particular, this object is achieved in that the transfer unit is a sample inlet for gas chromatographs with a sampling head and the assembly group is a sampling chamber having a liner therein, wherein its end opposite to the sampling head is adapted to receive the end of a gas chromatographic separating column. A temperature sensor, for example a thermocouple, measures the temperature directly at the liner thereby achieving that the measured value of the control mechanism is measured with a higher accuracy. It is advantageous if the liner is provided with a recess receiving the temperature sensor in close heat conducting contact with the outer wall of the liner. The measured temperature then corresponds even better to the temperature of the sample and carrier gas. Furthermore the width of the annular space can be kept small thereby achieving a better and quicker heat transfer to the liner.

Preferably, the assembly group has a cylindrical inner tube having the heater in the form of a heating coil wound thereon, and an outer tube mounted around said heating coil and which is tightly connected to the inner tube and the heating coil by a diameter reducing method. The assembly group with the heater consists of an inner tube and an outer tube which may have a relatively small thickness and thereby, a small thermal capacity, and wherein the heating coil can be tightly fixed. The assembly group with an inner and an outer tube and the heating coil in-between can be installed in one unit on an injector tube mounted around the sample chamber.

Alternatively, the heater can be tightly fixed to the sample chamber or be integrated therein.

Preferably, the wires of the heating coil are pressed flat during the application of the diameter reducing method in such a way that they have a plane contact with the inner tube. A better plane contact between the wires and the inner tube is ensured and thereby an improved heat transfer.

Furthermore, it is advantageous, if the inner tube consists of a material having a high thermal conductivity, such as brass. The outer tube and the injector tube preferably consist of a material having a small thermal conductivity, such as stainless steel.

Thereby, the temperature compensation in the brass layer is effected in a longitudinal direction. This is enabled by the thermal resistance of the stainless steel layer in a radial direction. Heat will prefer to flow in a longitudinal direction inside the brass material rather than immediately in a radial direction through stainless steel. However, as the layers are relatively thin having a small thermal capacity this procedure will not cause any considerable delay. It is also possible to use materials with good conductivity also. The small mass will cause a quick heat compensation.

The outer tube of the sample chamber preferably consists of a material having a small thermal conductivity such as stainless steel. Thereby, the heat loss towards the outside is reduced.

In a further modification of the invention, cooling medium is used for temperature control which flows through the space between the heating coil. Contrary to prior art devices, the sensor is not wound together with the heating coil, whereby a continuous space is generated which may be used for cooling medium. Preferably, the connection is heated by the heater.

Further modifications of the invention are subject matter of the sub claims. An embodiment of the invention is described below in greater detail with reference to the accompanying drawings.

DESCRIPTION OF THE EMBODIMENT

Figure 2:
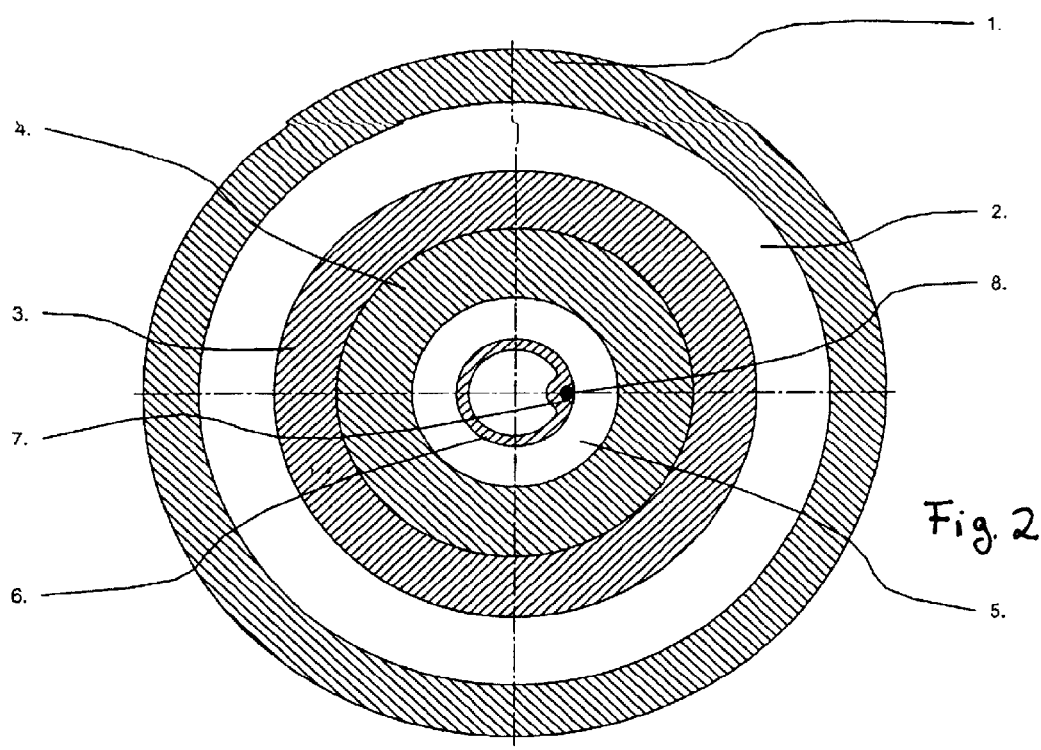
FIG. 2 schematically shows a cross section through the sample chamber and the liner of the sampling inlet of FIG. 1.
Figure 1:
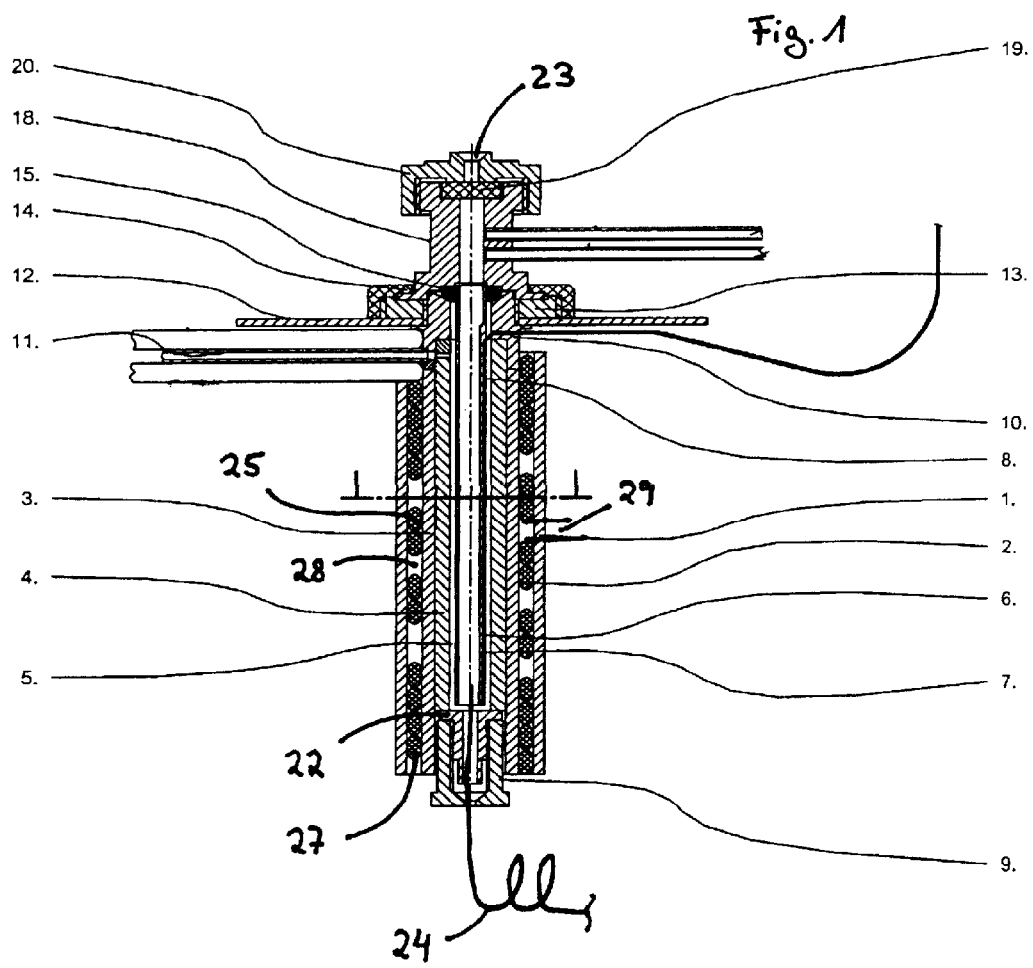
FIG. 1 is a longitudinal cross section of a sampling inlet for a gas chromatograph.

In FIG. 1, numeral 18 denotes a sampling head. The sampling head 18 is provided with a central inlet channel 23 closed by a septum 19. For introducing a liquid sample which is dissolved in a highly volatile solvent, the septum 19 is punctured by an injection needle of a syringe (not shown). The injection needle is introduced through the inlet channel 23 into a central glass liner 6. The sample with the solvent is discharged in this liner. Carrier gas is inserted into the inlet channel through a connection.

The liner 6 is heated according to a program. The liner 6 coaxially sits in a tube-shaped assembly group. The assembly group is provided with an inner tube 3 and an outer tube 1. A heating coil 2 is held between the inner tube 3 and the outer tube 1. The heating coil 2 is bifilar wound around the inner tube 3. The outer tube 1 is positioned on the inner tube 3 with the heating coil 2 and tightly fixed to the inner tube 3 and the heating coil 2 by a diameter reducing method. This diameter reducing method can be shrinking but also hammering, pressing or pulling. In such a way a cartridge-type body is generated wherein the heating coil is integrated.

With the diameter reducing method, the wire of the heating coil 2 is flattened as is indicated in FIG. 1. Thereby a plane contact is established between the inner tube 3 and the wire of the heating coil 2 and thereby the heat transfer is improved.

The inner tube 3 consists of a material with a good thermal conductivity, such as brass. The outer tube consists of a material with a low thermal conductivity, such as stainless steel. The assembly group is positioned on an injector tube 4 made of stainless steel. The liner 6 is arranged inside the injector tube 4.

An annular space 5 is formed between the injector tube 4 and the liner 6. A split connection 11 for removing evaporated solvent is connected to the annular space 5 near the inlet side end of the assembly group. The interior of the liner 6 is connected to the annular space 5 through its open outlet side end. An adapter 22 is provided at the outlet side end of the assembly group. The adapter 22 keeps the inlet end of a capillary column 24 coaxially to the liner 6 in such a way that the inlet end of the capillary column 24 extends into the outlet end of the liner 6.

The assembly group extends beyond the split connection 11 and the adapter 22, respectively, with the end 1 of the heat coil 2. The heat heating coil 2 is wound with larger distances in the middle section than in the ranges towards the ends as it is known from the prior art, in order to account for the increased heating power of the heat dissipation towards the ends 26 and 27 and to obtain a constant temperature over the entire length of the assembly. Furthermore, the wires of the heating coil have a larger diameter at the ends 1 than in the middle section 25. Thereby, the heating power in the ends extending over the split outlet 11 is reduced. The full heating power serves for heating the adapter 22 and a column connection nut 9.

A temperature sensor 8 is present in the annular space 5 between the liner 6 and the assembly group. Preferably, the temperature sensor 8 is a coated thermocouple of the Thermocoax®-type. The liner 6 has a longitudinal recess on one side accommodating the temperature sensor 8 in tight thermal contact with the outer wall of the liner 6.

A cooling medium may be introduced through a connection 29 into the space 28 between the bifilar coil of the heating coil 2 for cooling, if necessary.

The described assembly can be used also for thermal desorption in addition to sampling in gas chromatography. In this case a thermal desorption tube is used instead of a glass liner. The assembly can also be used for headspace.

The invention claimed is:

1. Transfer unit for analytic instruments, comprising
a tubular, cartridge-type assembly group in the form of a sampling chamber with an inner wall,
an electric heater for heating said assembly group according to a program,
a gas chromatographic separating column having two ends,
a liner inside said sampling chamber adapted to receive one of said ends of said gas chromatographic separating column, said liner designed in such a way that an annular space with an open outlet end is formed between said inner wall of said sampling chamber and said liner, and wherein said liner has an outside and an inside, said inside connected to said annular space through said open outlet end,
means for inserting carrier gas into the liner,
wherein a temperature sensor is arranged in said annular space,
wherein, said assembly group has a cylindrical inner tube and said heater has the form of a heating coil wound on said cylindrical inner tube, and
wherein said assembly group has an outer tube mounted around said heating coil which is tightly connected to said inner tube and said heating coil by a diameter reducing method.

2. Transfer unit according to claim 1, wherein said transfer unit is a sample inlet for gas chromatographs with a sampling head, said sample chamber of said transfer unit having two ends, wherein one of said ends is opposite to the sampling head and said end opposite to said sampling head is adapted to receive an end of said gas chromatographic separating column.

3. Transfer unit according to claim 2, wherein a split connection is provided for removing evaporated solvent.

4. Transfer unit according to claim 3, wherein said assembly group extends beyond the range of the split connection with an end of said heating coil.

5. Transfer unit according to claim 4, wherein said heating coil has wires, and said wires of said heating coil have a larger diameter at their ends than in their middle portion.

6. Transfer unit according to claim 2, wherein an adapter is installed at said end of said sample chamber opposite to the sampling head, wherein said adapter holds said separating column in such a way that its end extends into the liner.

7. Transfer unit according to claim 6, wherein said assembly group extends beyond the range of said adapter with the end of its said heating coil.

8. Transfer unit according to claim 1, wherein said heating coil has wires, said wires of said heating coil pressed flat during the application of said diameter reducing method in such a way that they have a plane contact with the inner tube.

9. Transfer unit according to claim 1, wherein said inner tube of said assembly group has an inner and an outer layer with respect to the tube axis, said inner and outer layer being connected and wherein said inner layer has a low thermal conductivity, and said outer layer consists of a material having a higher thermal conductivity.

10. Transfer unit according to claim 9, wherein said outer tube of said assembly group is made of a material having a low thermal conductivity.

11. Transfer unit according to claim 9, wherein said inner layer having a low thermal conductivity consists of stainless steel.

12. Transfer unit according to claim 9, wherein said outer layer having a higher thermal conductivity consists of brass.

13. Transfer unit according to claim 1, wherein said liner consists of glass.

14. Transfer unit according to claim 1, additionally including means for conducting cooling medium through a space between said heating coil for temperature control.

15. Transfer unit according to claim 1, wherein said liner consists of quartz.

16. Transfer unit for analytic instruments, comprising
a tubular, cartridge type assembly group in the form of a sampling chamber with an inner wall,
an electric heater for heating said assembly group according to a program,
a gas chromatographic separating column having two ends,
a liner inside said sampling chamber adapted to receive one of said ends of said gas chromatographic separating column, said liner designed in such a way that an annular space with an open outlet end is formed between said inner wall of said sampling chamber and said liner, and wherein said liner has an outside and an inside, said inside connected to said annular space through said open outlet end,
means for inserting carrier gas into the liner,
wherein a temperature sensor is arranged in said annular space, and
wherein said liner is provided with a recess receiving said temperature sensor in close heat conducting contact with said outside of said liner.

* * * * *